United States Patent
Zaveri et al.

(10) Patent No.: US 11,065,298 B1
(45) Date of Patent: Jul. 20, 2021

(54) COMPOSITIONS AND METHODS FOR TREATING OR PREVENTING VIRAL INFECTIONS

(71) Applicants: Chanda Zaveri, Rancho Palos Verdes, CA (US); Meng Teng Lim, Island East (HK)

(72) Inventors: Chanda Zaveri, Rancho Palos Verdes, CA (US); Meng Teng Lim, Island East (HK)

(*) Notice: Subject to any disclaimer, the term of this patent is extended or adjusted under 35 U.S.C. 154(b) by 0 days.

(21) Appl. No.: 16/896,092

(22) Filed: Jun. 8, 2020

Related U.S. Application Data

(60) Provisional application No. 63/015,376, filed on Apr. 24, 2020.

(51) Int. Cl.
| | |
|---|---|
| *A61K 38/10* | (2006.01) |
| *A61K 9/00* | (2006.01) |
| *A61P 31/14* | (2006.01) |
| *A61K 35/10* | (2015.01) |
| *A61P 31/22* | (2006.01) |
| *A61P 31/16* | (2006.01) |

(52) U.S. Cl.
CPC ............ *A61K 38/10* (2013.01); *A61K 9/0053* (2013.01); *A61K 35/10* (2013.01); *A61P 31/14* (2018.01); *A61P 31/16* (2018.01); *A61P 31/22* (2018.01)

(58) Field of Classification Search
None
See application file for complete search history.

(56) References Cited

PUBLICATIONS

Klöcking et al. "Medical Aspects and Applications of Humic Substances", Biopolymers for Medical and Pharmaceutical Applications, 2005, pp. 1-14 (Year: 2005).*
Ashely, "Warning Letter: NRP Organics Ltd" US Food and Drug Administration, 2020; obtained from https://www.fda.gov/inspections-compliance-enforcement-and-criminal-investigations/warning-letters/nrp-organics-ltd-606066-04082020 (Year: 2020).*
Raghunathan, "Multi-Millionaire Indian American Scientist Chanda Zaveris Has a Pill to Stave off Covid-19", 2020; obtained from https://www.indiawest.com (Year: 2020).*
"Broad Spectrum Antiviral Effectiveness of Natural and Synthetic Humates," National Institutes of Heath, white paper, Aug. 9, 2002, pp. 1-5.
"Humid Acid: Broad-Spectrum Efficacy," National Institutes of Health, white paper, Aug. 2001-Jan. 2002, pp. 1-30.
D. Chang et al., "Time Kinetics of Viral Clearance and Resolution of Symptoms in Novel Coronavirus Infection." Am. J. Respir. Crit. Care Med. 2020; 201(9): 1150-1152. doi:10.1164/rccm.202003-0524LE.
F. Schiller et al., "Results of a oriented clinical trial of ammonium humane for the local treatment of herpesvirus hominid (HVH) infections." Dermal. Monatsschr. Jul. 1979, 165(7) 505-509.
J. Neyts et al., "Poly(hydroxy)carboxylates as Selective Inhibitors of Cytomegalovirus and Herpes Simplex Virus Replication," Antiviral Chemistry & Chemotherapy, 3(4), 1992, pp. 215-222.

\* cited by examiner

*Primary Examiner* — Lianko G Garyu
(74) *Attorney, Agent, or Firm* — Elevated IP, LLC

(57) ABSTRACT

Compositions and methods disclosed herein may be used for treating or preventing viral infections. The compositions may be administered orally to subjects in need of preventative or therapeutic treatment and/or the compositions may be used to disinfect surfaces in order to prevent or limit the spread of disease through surface contact.

19 Claims, No Drawings

Specification includes a Sequence Listing.

COMPOSITIONS AND METHODS FOR TREATING OR PREVENTING VIRAL INFECTIONS

CROSS-REFERENCE TO RELATED APPLICATIONS

This application claims the benefit of and priority to U.S. Provisional patent application No. 63/015,376, filed Apr. 24, 2020, which is hereby incorporated by reference in its entirety.

INCORPORATION OF SEQUENCE LISTING

This document incorporates by reference herein an electronic sequence listing text file, which was filed in electronic format via EFS-Web with the application. The text file is named "9-20_US_Seq_Listing_ST25.txt," is 521 bytes, and was created on Jun. 8, 2020.

STATEMENT REGARDING FEDERALLY SPONSORED RESEARCH

None.

BACKGROUND

We are in the midst of a global pandemic caused by a highly contagious and lethal coronavirus (SARS-CoV-2, COVID-19) infecting a virgin population devoid of natural immunity. Massive research efforts to develop a vaccine are underway, but currently the only way to slow the spread of the disease is for people across the world to avoid contact with others whenever possible and to wear protective masks when they venture into public. These restrictions have taken a toll on people's livelihoods, mental states, relationships, and broader health. Accordingly, the need to find a composition with prophylactic and/or therapeutic efficacy against the novel coronavirus is urgent. And, to ensure we are not defenseless when faced with the next new virus it would be beneficial to develop a composition that is effective against a wide variety of viruses.

Humic acid (HA) refers to a mixture of acids formed after decomposition/humification of organic matter in soil, water, peat and sediment. The stable compounds in lignite or leonardite deposits that resist further decomposition and are soluble in alkaline media are referred to as humic acid. As early as 1992, researchers discovered the efficacy of humic acid against viruses. (J. Neyts et al., "Poly(Hydroxy)Carboxylates as Selective Inhibitors of Cytomegalovirus and Herpes Simplex Virus Replication," 3(4), Aug. 1, 1992, pages 215-222.) They hypothesized that the polyanionic form of HA, that is present in basic media, interacts with positively charged domains of viral envelope glycoproteins to block viral attachment to a cell surface. Since then, additional studies have shown that HA not only prevents HIV-1, HSV-1, HSV-2, VZV, EBV, H1N1 and H3N2 infections in multiple cell lines when administered prior to or at the same time as virus exposure, it also provides a therapeutic effect after cells have been infected. (Broad Spectrum Antiviral Effectiveness of Natural and Synthetic Humates, Virology Branch, Antiviral Research & Antimicrobial Chemistry Program, Division of Microbiology & Infectious Diseases, Screening & Testing Program for Antiviral, Immunomodulatory, Anti-tumor and/or Drug Delivery Activities, National Institutes of Allergy & Infectious Diseases, National Institute of Health, Aug. 9, 2002.) The same study showed that HA was not cytotoxic at levels at least as high as 100 µg/mL in vitro, and another study found that HA was non-toxic in vivo at concentrations up to 50 mg/kg. (Schiller, F. et al. Results of an oriented clinical trial of ammonium humate for the local treatment of herpesvirus *hominis* (HVH) infections. Dermatol. Monatsschr. 1979 July; 165(7): 505-9.) Thus, humic acid is a promising candidate for further research on compositions with prophylactic and/or therapeutic efficacy against viruses.

SUMMARY

Compositions and methods disclosed herein may be used for treating or preventing viral infections. The compositions may be administered orally to subjects in need of preventative or therapeutic treatment and/or the compositions may be used to disinfect surfaces in order to prevent or limit the spread of disease through surface contact.

In an aspect, a composition for treating or preventing a viral infection comprises humic acid and a peptide (CZV2.14) comprising a sequence of Gly-Glu-Pro-Pro-Pro-Gly-Lys-Pro-Ala-Lys-Asp-Ala-Gly-Lys (GEPPPGKPAKDAGK) (SEQ ID NO: 1).

In an embodiment, the peptide consists essentially of an amino acid sequence of Gly-Glu-Pro-Pro-Pro-Gly-Lys-Pro-Ala-Lys-Asp-Ala-Gly-Lys (SEQ ID NO: 1). In an embodiment, the peptide consists of an amino acid sequence of Gly-Glu-Pro-Pro-Pro-Gly-Lys-Pro-Ala-Lys-Asp-Ala-Gly-Lys (SEQ ID NO: 1).

In an embodiment, the humic acid and the peptide are covalently bound to one another, or the humic acid and the peptide are ionically bound to one another, or the humic acid and the peptide are electrostatically attracted to one another.

In an embodiment, a weight ratio of humic acid to peptide is between 500 and 100000, or between 5000 and 80000, or between 10000 and 70000, or between 25000 and 60000, or between 40000 and 50000. In an embodiment, a weight ratio of humic acid to peptide is about 50000 (e.g., 250 mg humic acid to 5 µg peptide per tablet).

In an embodiment a composition for treating or preventing a viral infection further comprises one or more pharmaceutical carriers, excipients, preservatives, colorants and/or diluents.

In an aspect, a method of treating or preventing a viral infection in vivo comprises administering to a subject a therapeutically effective amount of a humic acid and peptide composition disclosed herein.

In an embodiment, the therapeutically effective amount is between 20 mg/kg/day and 50 mg/kg/day, or between 25 mg/kg/day and 40 mg/kg/day, or is about 30 mg/kg/day. In an embodiment, the therapeutically effective amount is administered in portions once daily, twice daily or three times daily.

In an embodiment, the composition is administered orally. For example, the composition may be formulated as a capsule, a tablet, an emulsion, a tincture, a syrup, or a wet or dry food additive.

In an embodiment, the viral infection treated or prevented by the disclosed compositions is selected from the group consisting of Severe Acute Respiratory Syndrome (SARS), Middle East Respiratory Syndrome (MERS), human immunodeficiency virus (HIV), herpes simplex virus (HSV), cytomegalovirus (CMV), Varicella Zoster virus (VZV), Epstein-Barr virus (EBV), influenza, Hemorrhagic fever, Respiratory Syncytial Virus (RSV) and combinations thereof. In an embodiment, the viral infection is selected from the group consisting of SARS-CoV-2, HIV-1, HIV-2, HSV-1, HSV-2, H1N1, H3N2, RSV-2 and combinations thereof.

In an aspect, a method of disinfecting a surface comprises dispersing a humic acid and peptide composition disclosed herein in a solvent to create a mixture and contacting the surface with the mixture. In an embodiment, dispersing comprises dissolving, and in such case, a mixture is synonymous with a solution.

In an embodiment, the step of contacting comprises wiping, immersing, spraying, dipping or combinations thereof.

In an embodiment, the solvent has a neutral pH, an acidic pH or a basic pH. A suitable solvent may, for example, be selected from the group consisting of water, methanol, ethanol, n-propanol, isopropanol, butanol, octanols, acetonitrile, benzyl alcohol, ethylene glycol, propylene glycol, dioxane, tetrahydrofuran, methyl acetate, ethyl acetate, acetone, potassium hydroxide, amines, amino alcohols, phosphoric acid, hydrochloric acid, sulfuric acid, nitric acid, sulfonic acid, acetic acid, tartaric acid, lactic acid, citric acid, salicylic acid, $C_5$-$C_{20}$ carboxylic acids, and combinations thereof.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of this description.

An "amino acid" is a molecular building block of protein. An "amino acid residue" is the simplest discreet unit or monomer of a protein chain or peptide.

In the context of this specification, the term "substantially purified" refers to a state of purity that is at least 50%, preferably at least 70%, more preferably at least 85%, and still more preferably at least 95%, and in which a peptide having physiological activity is present in the substantial absence of other peptides or proteins having physiological activity.

Peptides having conservative amino acid substitutions are within the scope of the present invention. It is a well-established principle of protein and peptide chemistry that certain amino acid substitutions, called "conservative" amino acid substitutions, can frequently be made in a protein or a peptide without altering either the conformation or the function of the protein or peptide. Such changes include substituting any of isoleucine (I), valine (V), and leucine (L) for any other of these amino acids; aspartic acid (D) for glutamic acid (E) and vice versa; glutamine (0) for asparagine (N) and vice versa; and serine (5) for threonine (T) and vice versa. The above-mentioned substitutions are not the only amino acid substitutions that can be considered "conservative". Other substitutions can also be considered conservative, depending on the environment of the particular amino acid. For example, glycine (G) and alanine (A) can frequently be interchangeable, as can alanine (A) and valine (V). Methionine (M), which is relatively hydrophobic, can frequently be interchanged with leucine (L) and isoleucine (I), and sometimes with valine (V). Lysine (K) and arginine (R) are frequently interchangeable in locations in which the significant feature of the amino acid residue is its charge and the differing pK's of these two amino acid residues are not significant. Cysteine (C) can frequently be replaced by serine (5) when cysteine's capacity to form disulfide bonds is either undesirable or unneeded. Still other changes can be considered "conservative" in particular environments.

Nucleic Acids Encoding the Peptides

Peptides disclosed herein may be encoded by isolated nucleic acids. As used herein, the term "nucleic acid" includes both DNA and RNA and both single-stranded and double-stranded forms; if double-stranded, DNA-RNA hybrids are also included. Recitation of a single-stranded nucleic acid sequence also includes its complement according to the generally accepted Watson-Crick rules for base pairing. Nucleic acids encoding these peptides can either be DNA or RNA; however, in many applications, DNA is preferred.

The term "isolated" is used herein to indicate that the nucleic acids are present in substantial isolation from nucleic acid molecules that do not encode a peptide disclosed herein. In the context of this specification, the term "isolated" refers to a state of purity that is at least 50%, preferably at least 70%, more preferably at least 85%, and still more preferably at least 95%.

However, nucleic acids can be incorporated into larger nucleic acid molecules such as vectors for transfection of appropriate host cells and production of a peptide, and the term "isolated" is not to be interpreted to preclude this incorporation into larger, genetically-engineered molecules not occurring in nature.

The sequence of the nucleic acids is chosen according to the conventional triplet genetic code to encode the amino acid sequence of the particular peptides. Because the genetic code, which specifies amino acids by triplet codons in the nucleic acid sequence, is degenerate, and many amino acids are specified by more than one codon, all possible alternatives of codons can be used. However, in some cases, the efficiency of transcription and/or translation of the nucleic acid sequences can be affected by the codon selection. In such cases, it is preferred to use codons that provide increased efficiency of transcription and/or translation of the nucleic acid sequences.

Vectors and Host Cells

A vector comprising a DNA operably linked to at least one control element that influences the expression of the DNA is also contemplated. These control elements can be promoters, operators, enhancers, or other nucleic acid sequences that affect the expression of the DNA. The vector can be derived from either prokaryotic or eukaryotic sources. The vector can comprise sequences of chromosomal, non-chromosomal, or synthetic DNA sequences. Typically, these vectors include one or more cloning sites that contain restriction endonuclease sequences that are readily cleavable by specific restriction endonucleases. It is generally preferred that these restriction endonucleases yield cohesive or "sticky" ends for more efficient cloning of the desired sequence. Some suitable prokaryotic cloning vectors include plasm ids from *Escherichia coli*, such as colE1, pCR1, pBR322, pMB9, pUC, pKSM, or RP4. Prokaryotic vectors also include derivatives of bacteriophage DNA such as M13 and other filamentous single-stranded DNA phages. Other vectors, such as baculovirus vectors, can be used.

Examples of useful expression controlled sequences are the lac system, the trp system, the tac system, the trc system, major operator and promoter regions of bacteriophage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters of SV40 and other sequences known to control the expression of genes of prokaryotic or eukaryotic cells and their viruses or combinations thereof. Vectors useful in yeast are available. A suitable example is the 2p plasmid. Vectors for use in animal cells are also known. These vectors include derivatives of SV40, adenovirus, retrovirus-derived DNA sequences, and shuttle vectors derived from combinations of functional mammalian vectors, such as those described above, and functional plasmids and phage DNA. Another suitable vector is the baculovirus vector. In general, however, it is preferred to use a vector that is suitable for expression in *E. coli*.

Vectors are inserted into a host cell for expression. Typically, these vectors are inserted into a host cell by methods well known in the art, such as transfection, transformation, electroporation, direct injection of the DNA, lipofection, and other well-understood methods. The method to be used can be chosen according to the host cells selected and the size and conformation of the DNA. Some useful expression host cells include well-known prokaryotic and eukaryotic cells. Some suitable prokaryotic hosts include, for example, *E. coli*, such as *E. coli* SG-936, *E. coli* HB101, *E. coli* W3110, *E. coli* •1776, *E. coli* •0.2282, *E. coli* DHI, and *E. coli* MRCI. Other bacterial and fungal host cells could be used, such as *Pseudomonas, Bacillus* species, such as *Bacillus subtilis*, and *Streptomyces*. Other host cells that can be used are eukaryotic cells such as yeast and other fungi, insect cells, animal cells, such as COS cells and CHO cells, human cells, and plant cells in tissue culture.

Methods of Preparation of Peptides

Solid-State Peptide Synthesis

Peptides can be synthesized by standard solid-state peptide synthesis methods, such as those described in M. Bodanszky, "Principles of Peptide Synthesis" (Springer-Verlag, Berlin, 2d ed., 1993). This involves synthesis on an insoluble polymer such as a styrene-divinylbenzene copolymer that is derivatized. The sequence of reactions used is standard.

Genetic Engineering

Peptides can be prepared by genetic engineering. In general, a method of producing a substantially purified peptide having a physiological activity comprises the steps of: (1) culturing a host cell transfected with a vector comprising DNA encoding the peptide operably linked to at least one control element that influences the expression of the DNA; and (2) isolating the peptide produced by the host cell to produce the substantially purified peptide.

Expression methods are described in, e.g., D. V. Goeddel, "Gene Expression Technology" (Academic Press, San Diego, 1991). In general, such methods are well known in the art.

Once expressed, the peptides can be isolated by standard protein isolation techniques including ion-exchange chromatography on resins such as diethylaminoethylcellulose or carboxymethylcellulose, chromatography on size exclusion media (gel filtration), isoelectric focusing, chromatofocusing, and other standard methods, such as those described in R. K. Scopes, "Protein Purification: Principles and Practice" (3rd Ed., Springer-Verlag, New York, 1994).

If polyclonal or monoclonal antibodies are prepared for these peptides, these antibodies can be used in affinity chromatography by standard methods such as those described in the above-identified Scopes book. Such methods for the preparation of polyclonal antibodies or monoclonal antibodies are well known in the art and need not be described in further detail here. In general, polyclonal antibodies are produced by injecting the peptides, with or without a suitable adjuvant such as Freund's complete adjuvant, into an antibody-producing mammal such as a rat, a rabbit, a sheep, or a goat. The peptide can be coupled to a carrier protein such as keyhole limpet hemocyanin. Once polyclonal antibodies are produced, cells producing such polyclonal antibodies can be fused with appropriate fusion partners by standard techniques to yield hybridomas producing monoclonal antibodies of defined specificity.

Method of Preparation of Humic Acid

Humic acid can be extracted from any material containing well-decomposed organic matter by treating the material with a solution of sodium hydroxide to dissolve the organic matter. Acid is then added dropwise to lower the pH to about 2, and the organic material that flocculates to the top can be mechanically separated from the liquid portion. The flocculated material is humic acid, which when dried, and optionally crushed and sized, forms a black solid called humate.

Humic acid can also be purchased from commercial suppliers.

Methods of Use

Humic acid and peptide compositions disclosed herein can be used in multiple ways. When used as pharmaceuticals, the compositions are typically administered orally in the form of a capsule, a tablet, an emulsion, a tincture, a syrup or a food additive. When used as a surface disinfectant, the compositions are typically dissolved or dispersed in a solvent to create a solution or mixture that is used to contact (e.g., wipe, spray or otherwise immerse) the surface.

A preferred pharmaceutical dose is about 30 mg/kg/day of humic acid and peptide in a weight ratio of about 50000. The dosages to be administered can be determined by one of ordinary skill in the art depending on the clinical severity of the problem, the age and weight of the patient, the exposure of the patient to conditions that may affect the chance of infection, the existence or nonexistence of underlying systemic problems such as diabetes, impaired circulation, and immunocompromised status, and other pharmacokinetic factors generally understood in the art, such as liver and kidney metabolism. The interrelationship of dosages for animals of various sizes and species and humans based on mg/kg is described by E. J. Freireich et al., "Quantitative Comparison of Toxicity of Anticancer Agents in Mouse, Rat, Hamster, Dog, Monkey and Man," Cancer Chemother. Rep. 50: 219-244 (1966). Adjustments in the dosage regimen can be made to optimize the preventative and/or therapeutic response. Doses can be divided and administered on a daily basis or the dose can be reduced proportionally depending on the therapeutic situation.

The active ingredients are often mixed with diluents or excipients that are physiologically tolerable and compatible with the active ingredients. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as Remington's Pharmaceutical Sciences, Mack Publishing Co. Easton, Pa. (1970).

Methods according to the present invention can be used to treat humans or socially or economically important animal species such as dogs, cats, horses, sheep, cows, goats, or pigs. Methods according to the present invention are not limited to use in humans.

Pharmaceutical Compositions

In general, a pharmaceutical composition as disclosed herein comprises: (1) humic acid; (2) a peptide comprising SEQ ID NO: 1; and, optionally, (3) a pharmaceutically acceptable carrier.

The physiologically effective quantity can be determined by one of ordinary skill in the art with reference to the dosages described above.

Conventional pharmaceutically acceptable carriers known in the art can include alcohols, e.g., ethyl alcohol, serum proteins, cholesterol, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents; vegetable oils, and conventional anti-bacterial or anti-fungal agents, such as parabens, chlorobutanol, phenol, sorbic acid, thimerosal; and the like. A pharmaceutically acceptable carrier meets industry standards for sterility, isotonicity, stability, and non-pyrogenicity.

The invention is illustrated by the following Examples. These Examples are for illustrative purposes only and are not intended to limit the invention.

EXAMPLES

Example 1: Efficacy of humic acid and peptide (CZV2.14) compositions on influenza symptoms This Example compares the efficacy of compositions comprising humic acid+peptide on influenza symptoms compared to results of humic acid alone, using the protocol described in Amar, S., Escovar, Y., "A Randomized, Double-Blind, Placebo-Controlled, Parallel-Group Pilot Study to Investigate the Effects of Humic Acid on Symptoms of Influenza. 2 Sept. 2018.

Twenty participants were split into a treatment group of 10 and a placebo group of 10. Tables 1-4 show the results of the humic acid study versus the humic acid +peptide study.

TABLE 1

Influenza symptom scores.

| Symptom | HA Group n = 19 | Placebo (HA Study) n = 18 | HA + Peptide n = 10 | Placebo (HA + Peptide Study) n = 10 |
|---|---|---|---|---|
| Cough | 61.9 | 36.8 | 79.2 | 32.8 |
| Fever | 91.7 | 81.8 | 93.4 | 79.2 |
| Myalgia/arthralgia | 86.4 | 62.5 | 90.5 | 60.7 |
| Chills | 91.7 | 66.7 | 92.6 | 59.5 |
| Fatigue | 80.0 | 54.5 | 83 | 51 |
| Rhinorrhea | 66.7 | 62.5 | 68.9 | 59.5 |

TABLE 2

Percent change in TNF-α and IL-8 markers at Week 2.

| Marker | HA Group n = 19 | Placebo (HA Study) n = 18 | HA + Peptide n = 10 | Placebo (HA + Peptide Study) n = 10 |
|---|---|---|---|---|
| TNF-α | −26.7% | −7.1% | −47.1% | −1.6% |
| IL-8 | −3.2% | −10.2% | −35% | 8.3% |

TABLE 3

Visual analog scale (VAS) from week-to-week.

| Time | HA Group n = 19 | Placebo (HA Study) n = 18 | HA + Peptide n = 10 | Placebo (HA + Peptide Study) n = 10 |
|---|---|---|---|---|
| Week 1 | 64% | 54% | 82.7% | 35.9% |
| Week 2 | 107% | 76% | 120.8% | 65.5% |
| Progress Week 1 to 2 | 43% | 22% | 38.1% | 29.6% |
| 40-60 y/o | 164% | 70.3% | — | — |

Psychometric response scale used for the study: Wewers et al., 1994.

An augmented improvement in VAS scores was noted in HA+peptide versus HA alone. In the HA alone group, greater severity of symptoms at baseline was observed with lower VAS scores.

A statistically significant increase in VAS score was demonstrated from baseline to Week 1 and Week 2 for subjects in the HA+peptide and placebo group (p <1=0.001) with a greater increase found from screening to Week 1 and 2 observed in subjects on HA+peptide as compared with placebo.

TABLE 4

Percent change in CD4+ and CD8+ markers at Week 2.

| Time | HA Group n = 19 | Placebo (HA Study) n = 18 | HA + Peptide n = 10 | Placebo (HA + Peptide Study) n = 10 |
|---|---|---|---|---|
| CD4+ | 2.8% | −3.1% | 73.9% | −3.1% |
| CD8+ | 1.4% | −11% | −5.1% | −0.6% |

CD4+ and CD8+ T-cells are useful biological marks for compromised immunocompetence and also for identifying insufficient antibody responses in the body. Researchers have found that many individuals have heterosubtype-specific CD4+ and CD8+ T-cells that help recognize conserved internal epitopes common to different serotypes; and, in the presence of such heterosubtypic T-cells, immunity, severity of disease, and duration of infection are reduced in individuals with flu. In the current study, the CD4+ and CD8+ lymphocyte T-cell counts in serum in subjects treated either with humic acid or placebo were measured after two weeks of treatment. Although there were no statistically significant differences, subjects on humic acid supplementation showed a 3% increase in absolute CD4+ cell counts from Screening to Week 2, whereas subjects on placebo showed a 3% decrease in CD4+ cell count. The finding that humic acid treatment in fact increased both CD4+ and CD8+ cells in this study suggests that it may play a role in modulating the human immune system response.

Example 2: In Vitro Evaluation of Anti-Viral Properties of Humic Acid and Peptide (CZV2.14)

A peptide (CZV2.14) comprising a sequence of Gly-Glu-Pro-Pro-Pro-Gly-Lys-Pro-Ala-Lys-Asp-Ala-Gly-Lys (SEQ ID NO: 1) is mixed with humic acid. An in vitro evaluation of the anti-viral properties of humic acid and polypeptide showed 100% viricidal activity against HSV-1 by day 3 and 60% viricidal activity against HSV-2 by day 3, as measured by plaque assay. Additionally, viricidal attachment inhibition was total (100%) against CMV and RSV-2 by day 3, as measured by virus yield assay. Without being bound by theory, it is believed that the peptide portion of the HA+CZV2.14 mixture binds to the spike protein (S-glycoprotein) of the virus and HA associates with the peptide (e.g., via electrostatic attraction) to create a humic acid "shell" around the virus, thereby chemically and physically blocking the virus's access to the cell and preventing infection.

Example 3: In Vivo Evaluation of Compositions Comprising Humic Acid and Peptide (CZV2.14)

Case #1
Singapore, February 2020: Family of 6 transported to hospital by ambulance and hospitalized, ages 20-54. All test positive for COVID-19.
Assay—24-hour processing window (PCR)
Treatment: 2 tablets or capsules of a composition comprising humic acid and a peptide comprising SEQ ID NO: 1 three times per day for 3 days
Discharge criteria—negative assay ×2, separated by 24 hours
First assay, 24 hours after initial treatment—negative
Second assay, 48 hours after initial treatment—negative
All family members discharged from hospital day #3 without complications
Case #2
Hong Kong, March/April 2020:
Background: Center Manager 1 (CM1) was exposed to a client with known COVID-19 infection at Distributor's business location. CM1 was taking humic acid and CZV2.14 product (Product) and did not get sick, but a co-worker who was known not to be taking Product (CM2) and co-mingled with CM1 and client did become symptomatic with fever, chills and emesis. She ultimately tested positive for COVID-19 and was hospitalized.
Hospital Course: CM2 declined to take Product in hospital because her primary treatment provider was treating with another medication and she was concerned about an unintended interaction; however, symptoms were deteriorating. Distributor obtained consent from CM2 to start Product on Apr. 2, 2020 at treatment dose, 3 tablets three times daily. Twenty-four hours after completing an initial treatment dose, fever was resolved. As of Apr. 4, 2020, CM2 was asymptomatic.
Note: Hong Kong practice is to publish the names of those infected with COVID-19 in the public record. CM2's information was published on Apr. 2, 2020.
Employer Response: Distributor became aware of CM2's infection on Mar. 31, 2020 and closed local operation for 4 days. At this juncture, all employees were instructed to take a treatment dose of Product, 3 tablets three times daily. Distributor is performing PCR tests on all employees prior to their return to work. All employees are also part of a nightly webinar where they can learn about COVID-19 and ask questions about Product in order to earn compliance with Product prophylactic dosing.
Product Instructions
Prophylactic directions: Take 1 tablet/capsule twice daily
Prophylactic directions with morbidity: Take 1 tablet/capsule 3 times daily
Chronic Disease—diabetic, heart disease
Autoimmune Disease—rheumatoid arthritis, IBD, lupus
Overfat
Genomic Predisposition (NLRP3, CCL2, IL-1A)
Treatment, COVID-19(+): Take 2 tablets/capsules by mouth three times daily
Treatment, COVID-19(+) with morbidity: Take 3 tablets/capsules by mouth three times daily Example 4: Clinical Data from the United States Twenty SARS-CoV2 positive patients were treated with compositions comprising humic acid (HA) and peptide (CZV2.14) at various dosages. The results of the study are presented below.

TABLE 5

Demographics & Disposition

| Case No. | Age (years) | Gender | IgM Antibody Assay | Symptomatic | Asymptomatic |
|---|---|---|---|---|---|
| 1 | 58 | F | + | + | |
| 2 | 72 | M | + | + | |
| 3 | 39 | M | + | | + |
| 4 | 61 | F | + | + | |
| 5 | 64 | M | + | + | |
| 6 | 39 | M | + | | + |
| 7 | 26 | M | + | + | |
| 8 | 49 | F | + | | + |
| 9 | 50 | M | + | + | |
| 10 | 43 | M | + | + | |
| 11 | 32 | F | + | + | |
| 12 | 67 | F | + | + | |
| 13 | 67 | F | + | + | |
| 14 | 29 | M | + | + | |
| 15 | 19 | F | + | + | |
| 16 | 43 | M | + | | + |
| 17 | 41 | F | + | + | |
| 18 | 72 | M | + | + | |
| 19 | 23 | M | + | | + |
| 20 | 54 | M | + | | + |

TABLE 6

Symptoms

| Case No. | Fever/$T_{MAX}$ (°F.) | Cough | Body ache | Dyspnea | Fatigue | Headache | Nausea/Emesis | Chest pain | Anorexia |
|---|---|---|---|---|---|---|---|---|---|
| 1 | +/103 | | | | | | | | |
| 2 | +/102 | + | + | | | | | | |
| 4 | + | + | | + | | + | +/+ | | |
| 5 | + | + | + | | + | | +/− | | |
| 7 | + | + | + | | | | −/+ | | |
| 9 | +/102 | + | + | | + | | −/+ | | + |
| 10 | + | + | + | | + | | −/+ | | |
| 11 | +/103 | | + | | | + | −/+ | + | |
| 12 | +/102 | + | + | | | + | −/+ | | |
| 13 | +/103 | + | | | + | + | −/+ | + | + |
| 14 | | + | + | | | | | | |
| 15 | +/102.2 | + | + | | | | −/+ | | |
| 17 | + | + | | + | | | | | |
| 18 | +/101 | + | | + | | | | | |

TABLE 7

Treatment Endpoints

| Case No. | Dose | Baseline status[5] (S vs. AS) | Interval[1] $T_{MAX}$-AF (days) | Treatment Interval (days) | Antibody Conversion[4] (IgM to IgG) | Residual Symptoms |
|---|---|---|---|---|---|---|
| 1 | 500 mg tid[2] | S | 6 | 6 | 6 | — |
| 2 | 750 mg tid | S | 4 | 4 | 4 | — |
| 3 | 250 mg bid | AS | | 2 | 4 | — |
| 4 | 500 mg tid | S | 6 | 4 | 5 | — |
| 5 | 500 mg tid | S | | 7 | 6 | — |
| 6 | 500 mg tid | AS | | 3 | 3 | — |
| 7 | 750 mg tid | S | | 5 | 4 | — |
| 8 | 500 mg tid | AS | | 4 | 2 | — |
| 9 | 750 mg tid, tapered[3] | S | | 5 | 4 | — |
| 10 | 500mg tid | S | | 4 | 3 | — |
| 11 | 750 mg tid, tapered[3] | S | 4 | 4 | 3 | — |
| 12 | 750 mg tid, tapered[3] | S | 5 | 6 | 6 | — |
| 13 | 750 mg tid, tapered[3] | S | 6 | 8 | 7 | Fatigue |
| 14 | 500 mg tid | S | | 5 | 4 | — |
| 15 | 500 mg tid | S | 5 | 5 | 4 | — |
| 16 | 500 mg tid | AS | | 6 | 5 | — |
| 17 | 750 mg tid | S | | 6 | 6 | — |
| 18 | 750 mg tid | S | 3 | 5 | 3 | — |
| 19 | 750 mg tid, tapered[3] | AS | | 4 | 3 | — |
| 20 | 500 mg tid | AS | | 4 | 5 | — |

[1]Peak fever = Day 1; AF = afebrile = temperature is 98.6° F. (37° C.) or less
[2]tid = three times daily
[3]Tapered = 750 mg tid × 1-4 days, 500 mg bid × 1-3 days, 250 mg tid × 1-2 days
[4]Initial date of COVID-19 Ab + status = Day 0
[5]S = symptomatic, AS = asymptomatic

TABLE 8

Treatment Dates

| Case No. | Treatment Interval (days) | Initial | Final |
|---|---|---|---|
| 1 | 6 | Mar. 27, 2020 | Apr. 1, 2020 |
| 2 | 4 | Mar. 17, 2020 | Mar. 20, 2020 |
| 3 | 2 | Apr. 6, 2020 | Apr. 8, 2020 |
| 4 | 4 | Apr. 6, 2020 | Apr. 9, 2020 |
| 5 | 7 | Apr. 7, 2020 | Apr. 13, 2020 |
| 6 | 3 | Mar. 19, 2020 | Mar. 21, 2020 |
| 7 | 5 | Mar. 22, 2020 | Mar. 26, 2020 |
| 8 | 4 | Apr. 23, 2020 | Apr. 26, 2020 |
| 9 | 5 | Apr. 22, 2020 | Apr. 26, 2020 |
| 10 | 4 | Apr. 1, 2020 | Apr. 3, 2020 |
| 11 | 4 | Apr. 21, 2020 | Apr. 24, 2020 |
| 12 | 6 | Apr. 17, 2020 | Apr. 22, 2020 |
| 13 | 8 | Apr. 13, 2020 | Apr. 20, 2020 |
| 14 | 5 | Apr. 4, 2020 | Apr. 8, 2020 |
| 15 | 5 | Apr. 7, 2020 | Apr. 11, 2020 |
| 16 | 6 | Apr. 13, 2020 | Apr. 18, 2020 |
| 17 | 6 | Apr. 9, 2020 | Apr. 14, 2020 |
| 18 | 5 | Apr. 14, 2020 | Apr. 18, 2020 |
| 19 | 4 | Apr. 4, 2020 | Apr. 7, 2020 |
| 20 | 4 | Apr. 1, 2020 | Apr. 4, 2020 |

TABLE 9

Kinetics comparison against published data adjusted for age range

| | PLA General Hospital Beijing, China Jan. 28-Feb. 9, 2020[1] | HA + Peptide Case Studies United States |
|---|---|---|
| N (range) | 16 | 20 |
| Age (years) | 35.5 (24-43) | 47.4 (19-72) |
| Number hospitalized | 16 | 0 |
| Days of hospitalization | 6.5 (5.25-11) | Not applicable |
| Number of asymptomatic individuals with viral positivity | 0 | 6 |
| Days from onset of symptoms to resolution of symptoms | 8 (6.25-11.5) | — |
| Days from start of treatment to resolution of symptoms | — | 4.7 (3-8), with 1 exclusion due to residual symptoms after treatment, ages 19-72 4.3 (2-6), ages 24-43, n = 8 |
| Days from virus positivity to virus negativity | 5.5(4-8) | 4.35 (2-7), ages 19-72 4.0 (3-6), ages 24-43, n = 8 |
| Number of individuals with residual symptoms after reaching virus negativity | 8 out of 16 | 1 out of 20, n = 20 1 out of 14, n = 14 (Asymptomatic subgroup removed) |
| SYMPTOMS | | |
| | n = 16 | n = 14 |
| Cough N, % | 14 (87%) | 12 (86%) |
| Dyspnea N, % | 2 (12.5%) | 3 (21%) |
| Fever N, % | 14 (87.5%) | 13 (93%) |
| Febrile Days, Mean & Range | 6.5 (5-8) | 4.8 (3-6), n = 8 |
| Nausea/Emesis N, % | 2 (12.5%) (nausea only) | 9 (64%) |
| Fatigue N, % | — | 4 (29%) |
| Headache N, % | — | 4 (29%) |

[1]Chang D. et al. Time Kinetics of Viral Clearance and Resolution of Symptoms in Novel Coronavirus Infection. Am J Respir Crit Care Med. 2020; 201(9):1150-1152. doi:10.1164/rccm .202003-0524LE Observations and Conclusions The patient population reported by Chang was hospitalized. The HA+Peptide group was treated in an ambulatory setting. The standard of practice in China at the time of the study was to quarantine infected individuals by hospitalizing them. Regardless, symptoms between the two studies suggests that they were reasonably matched (e.g. fever, cough and dyspnea); however, age range was broader for the HA+Peptide group (19-72 years) vs. Chang (24-43 years).

High fever (greater than or equal to 102° F.) was recorded in 7 individuals in the HA+Peptide group. Five of these individuals were greater than 50 years of age. One individual (age 67) experienced residual symptoms in the HA+Peptide group versus 8 of 16 reported by Chang.

Fifty percent of the population in Chang experienced residual symptoms after achieving COVID negative status. Within the HA+Peptide group, 7.1% experienced residual symptoms after adjusting for the 6 individuals who experienced an asymptomatic clinical course.

Observation #1: Nine individuals in the HA+Peptide group were 50 years of age or older. Reduction of TNF-α (and thus IL-6) in the HA+Peptide group likely provided for a more rapid clinical de-escalation of the viral inflammatory response.

Observation #2: One would have expected more residual complaints from the 9 individuals greater than 50 years of age in the HA+Peptide group given changes in physiologic resilience with age. The anti-inflammatory activity of HA+Peptide, in addition to its ability to augment the immune system, likely contributed to this improved outcome.

Individuals using HA+Peptide between the ages of 24-43 reached virus negativity 1.5 days earlier than their age-matched cohort in Chang. The entire HA+Peptid group, between 19-72 years, achieved viral negativity nearly 1 day prior to the data reported by Chang.

Mean febrile days was 1.7 days less in the HA+Peptide group than in Chang. Similar findings were observed with HA+Peptide and influenza populations, TNF-α suppression and immune system augmentation likely plays into individuals' favorable recovery profile with HA+Peptide.

Statements Regarding Incorporation by Reference and Variations

All references cited throughout this application, for example patent documents including issued or granted patents or equivalents; patent application publications; and non-patent literature documents or other source material; are hereby incorporated by reference herein in their entireties, as though individually incorporated by reference.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods and devices useful for the present methods and devices can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a peptide" includes a plurality of such peptides and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

All art-known functional equivalents of materials and methods are intended to be included in this disclosure. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

What is claimed is:

1. A composition for reducing symptoms of influenza, the composition comprising:
   humic acid or a derivative thereof; and
   a peptide (CZV2.14) consisting of a sequence of Gly-Glu-Pro-Pro-Pro-Gly-Lys Pro-Ala-Lys-Asp-Ala-Gly-Lys (SEQ ID NO: 1).

2. The composition of claim 1, wherein the humic acid and the peptide are covalently bound to one another, or wherein the humic acid and the peptide are ionically bound to one another, or wherein the humic acid and the peptide are electrostatically attracted to one another.

3. The composition of claim 1, wherein a weight ratio of humic acid to peptide is between 500 and 100000.

4. The composition of claim 1 further comprising one or more pharmaceutical carriers, excipients, preservatives, colorants and/or diluents.

5. The composition of claim 1, wherein a weight ratio of humic acid to peptide is 50000.

6. A method of reducing symptoms of influenza in vivo, said method comprising administering to a subject in need thereof a therapeutically effective amount of the composition of claim 1.

7. The method of claim 6, wherein the humic acid and the peptide are covalently bound to one another, or wherein the humic acid and the peptide are ionically bound to one another, or wherein the humic acid and the peptide are electrostatically attracted to one another.

8. The method of claim 6, wherein the composition further comprises one or more pharmaceutical carriers, excipients, preservatives, colorants and/or diluents.

9. The method of claim 6, wherein the therapeutically effective amount is between 20 mg/kg/day and 50 mg/kg/day.

10. The method of claim 6, wherein the therapeutically effective amount is administered in portions once daily, twice daily or three times daily.

11. The method of claim 6, wherein the composition is administered orally.

12. The method of claim 11, wherein the composition is formulated as a capsule, a tablet, an emulsion, a tincture, a syrup or a food additive.

13. The method of claim 6, wherein a weight ratio of humic acid to peptide is between 500 and 100000.

14. The method of claim 6, wherein a weight ratio of humic acid to peptide is 50000.

15. The method of claim 6, wherein the therapeutically effective amount is tapered over time.

16. A method of disinfecting a surface comprising:
    dispersing a composition comprising humic acid and a derivative thereof and a peptide (CZV2.14) consisting of a sequence of Gly-Glu-Pro-Pro-Pro Gly-Lys-Pro-Ala-Lys-Asp-Ala-Gly-Lys (SEQ ID NO: 1) in a solvent to create a mixture; and
    contacting the surface with the mixture.

17. The method of claim 16, wherein the solvent has a neutral pH, an acidic pH or a basic pH.

18. The method of claim 16, wherein the solvent is selected from the group consisting of water, methanol, ethanol, n-propanol, isopropanol, butanol, octanols, acetonitrile, benzyl alcohol, ethylene glycol, propylene glycol, dioxane, tetrahydrofuran, methyl acetate, ethyl acetate, acetone, potassium hydroxide, amines, amino alcohols, phosphoric acid, hydrochloric acid, sulfuric acid, nitric acid, sulfonic acid, acetic acid, tartaric acid, lactic acid, citric acid, salicylic acid, C5-C20 carboxylic acids and combinations thereof.

19. The method of claim 16, wherein the step of contacting comprises wiping, immersing, spraying, dipping or combinations thereof.

* * * * *

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Gly Glu Pro Pro Pro Gly Lys Pro Ala Lys Asp Ala Gly Lys
1               5                   10
```